US00PP23554P2

(12) United States Plant Patent
Kordes

(10) Patent No.: US PP23,554 P2
(45) Date of Patent: Apr. 23, 2013

(54) HYBRID TEA ROSE PLANT NAMED 'KOR981457'

(50) Latin Name: *Rosa hybrida*
Varietal Denomination: KOR981457

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 13/136,638

(22) Filed: Aug. 5, 2011

(51) Int. Cl.
*A01H 5/00* (2006.01)

(52) U.S. Cl. ..... Plt./137

(58) Field of Classification Search ..... Plt./137, Plt./138

See application file for complete search history.

*Primary Examiner* — Kent L Bell

(57) ABSTRACT

A new and distinct variety of rose with long lasting, novel pink flowers, and attractive foliage with good disease resistance. It exhibits vigorous growth and an upright habit with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KOR981457'.

CROSS REFERENCES AND FEDERAL R&D STATEMENT

There are no cross referenced or related applications. This variety was developed without the aid of any research grant.

The new variety of rose plant of the present invention originated from a controlled crossing in a breeding program of two distinct parents during the summer of 1998. The crossing was between an 'un-named seedling' and an 'un-named seedling'.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KOR981457'.

SUMMARY OF THE INVENTION

The new rose plant may be distinguished from its seed parent, an 'un-named seedling', by the following combination of characteristics:

1. The fragrance of 'KOR981457' is strong while the fragrance of the seed parent is light.
2. The flower color of 'KOR981457' is pink while the flower color of the seed parent is amber yellow.

The new rose plant may be distinguished from its pollen parent, an 'un-named seedling' by the following combination of characteristics:

1. The flower color of 'KOR981457' is pink while the flower color of the pollen parent is apricot.
2. The petal edge of 'KOR981457' is entire while the petal edge of the pollen parent is incised.

The objective of the hybridization was to create a new and distinct rose plant with unique qualities, such as:

1. Uniform growth and flowering;
2. Abundant blooms with long vase life;
3. Long stems and foliage; and
3. Resistance to diseases encountered in commercial cut flower production.

This combination of qualities is not present in prior rose cultivars known to the inventor. These objectives have been substantially achieved and in that distinguish 'KOR981457' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KOR981457' was selected in May, 1999 from the seedling beds to be asexually propagated for further evaluation. The first asexual propagation of 'KOR981457' was done by budding to seedling understocks in July, 1999 at the inventor's nursery in Offenseth-Sparrieshoop, Germany.

This initial and other subsequent propagations conducted in controlled environments demonstrate that 'KOR981457' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KOR981457'.

DETAILED BOTANICAL DESCRIPTION

The following is a description of 'KOR981457', as observed growing in July, 2011 in a nursery in Jackson County, Oreg. on plants of 3 years of age. Color references are made using The Royal Horticultural Society (London, England) Colour Chart, 2001 except where common terms of color are used.

For a comparison, several physical characteristics of the rose variety 'KOR020424', a rose variety from the same inventor are compared to 'KOR981457' in Chart 1.

CHART 1

| Characteristic | 'KOR981457' | 'KOR020424' |
|---|---|---|
| Average sepal size: | 20-23 mm (l) × 6-8 mm (w). | 30 mm (l) × 12 mm (w). |
| Fragrance: | Strong. | Light. |
| Average leaf size: | 180 mm (l) × 120 mm (w). | 155 mm (l) × 75 mm (w). |

Parents:

*Seed parent*.—An 'un-named seedling'.

*Pollen parent*.—An 'un-named seedling'.

Classification:

*Botanical classification*.—*Rosa hybrida* 'KOR981457'.

*Commercial classification*.—Hybrid Tea.

FLOWER AND FLOWER BUD

Blooming habit: Recurrent.

Flower bud:

*Size*.—Upon opening, 28 mm in length from base of receptacle to end of bud and 25 mm diameter at its widest point.

*Bud form*.—Short. Pointed ovoid.

*Bud color*.—As sepals first unfold, bud color is Red-Purple Group 58D. When ¼ open, the upper surface of petals is Red-Purple Group 62D, and the lower surface is Red-Purple Group 62A. Guard Petals have intonations in middle and marginal zones of Red-Purple Group 71C and 71D.

*Sepals*.—Color: Upper surface Yellow-Green Group 146D. Lower surface Yellow-Green Group 146C with intonations of Greyed-Purple Group 185B. Size: Average 20-23 mm long×6-8 mm wide. Shape: Triangular. Weak foliaceous appendages on two of the five sepals. Apex: Apiculate. Base: Flat at union with receptacle. Quantity: Five. Surface texture: Upper side: Pubescent. Lower surface: Light pubescence. Margins: Pubescent.

Receptacle:

*Surface*.—Light pubescence.

*Color*.—Yellow-Green Group 146C.

*Shape*.—Funnel-shaped.

*Size*.—6-7 mm (h)×6 mm (w).

Peduncle:

*Surface*.—With stipitate glands.

*Length*.—65 to 70 mm average length.

*Diameter*.—2.0 to 2.5 mm average diameter.

*Color*.—Yellow-Green Group 146C with strong intonations of Greyed-Red Group 182B.

*Strength*.—Strong.

*Borne*.—Multiple flower buds per stem, generally 1 to 5.

Flower bloom:

*Fragrance*.—Strong.

*Duration*.—On the plant 8-10 days. Long lasting. As a cut flower, 7-8 days. Senesced petals drop away cleanly.

*Size*.—Medium sized for a hybrid tea rose. When open, the average flower diameter is 80 mm and the average flower height is 30 mm.

*Form*.—Shape of flower when viewed from the side: Upon opening, upper part: Flat. Upon opening, lower part: Flat. Open flower, upper part: Flat. Open flower, lower part: Concave.

Color:

*Upon opening, petals*.—Outermost petals: Outer Side: White Group N155C. Inner Side: Red Group 49D. Innermost petals: Outer Side: Red Group 55D. Inner Side: Red Group 56D.

*Upon opening, basal petal spots*.—Basal petal spot, outermost petals: Outer Side: Yellow Group 2C. Inner Side: Yellow Group 2D. Basal petal spot, innermost petals: Outer Side: Yellow Group 2B. Inner Side: Yellow Group 2B.

*After opening, petals*.—Outermost petals: Outer Side: Red-Purple Group 62D. Inner Side: Red-Purple Group 69C. Innermost petals: Outer Side: Red-Purple Group 69C. Inner Side: Red-Purple Group 62C.

*After opening, basal petal spots*.—Basal petal spot, outermost petals: Outer Side: Green-Yellow Group 1C. Inner Side: Yellow Group 2D. Basal petal spot, innermost petals: Outer Side: Green-Yellow Group 1B. Inner Side: Yellow Group 2B.

General tonality: On open flower Red-Purple Group 62D. No change in the general tonality at the end of the 7$^{th}$ day. Afterwards, general tonality is Red-Purple Group 69C and 69D.

Petals:

*Petal count*.—Very double. Average Range: Approximately 60 petals under normal conditions.

*Petal reflex*.—Petals reflex strongly.

*Petal edge*.—Entire.

*Petal shape*.—Obtuse. Apex shape is obtuse. Shape of base is deltoid.

*Petal Size*.—35 mm (l)×25 mm (w). Interior petals are smaller with the average being 10 mm (l)×5-6 mm (w).

*Thickness*.—Average.

*Petal Arrangement*.—Quartered.

Petaloids:

*Petaloid count*.—Average of 10-20 per flower.

*Petaloid size*.—Petaloids are 12 mm (l)×3 mm (w).

*Petaloid color*.—Color of inner side is Red-Purple Group 73D. Color of outer side is Red-Purple Group 73D.

*Petaloid texture*.—Smooth.

*Margins*.—Entire. Smooth to undulated.

*Petaloid shape*.—Obovate. Apex: Obtuse. Base: Deltoid. Petaloids emanate from between the stamens and pistils as well as immediately outside the stamens.

Reproductive organs:

*Pistils*.—Average. Approximately 20 present. Stigmas: Location: Slightly superior in position to anthers. Color: Red Group 53C. Styles: Length: About 6 mm long. Color: Yellow-Green Group 145C.

*Stamens*.—Approximately 30 on average and regularly arranged. Anthers: Size: About 0.05 mm long. Pollen: Present in a limited quantity. Color: Greyed-Brown Group 199B. Filaments: Color: Yellow Group 10B. Length: About 3-4 mm.

THE PLANT

Growth: Vigorous.

Plant habit: Upright habit. When grown as a budded field grown plant, the average plant height is 100 cm and the average plant width is 60 cm.

Stems:

*Stem color*.—Juvenile wood: Yellow-Green Group 146C. Mature wood: Yellow-Green Group 146D. Anthocyanin present on both juvenile and mature wood. Greyed-Orange Group 176B.

*Stem surface*.—Juvenile wood: Smooth. Mature wood: Smooth.

Prickles: Present.

*Incidence*.—Average of 7-8 per each 10 cm of stem.

*Size*.—Average length: 6 mm.

*Color*.—Immature prickles: Greyed-Red Group 182B. Mature prickles: Greyed-Red Group 182C.

*Shape*.—Concave.

Leaves and leaflets: Normally 5 leaflets on normal leaves in middle of the stem.

*Venation pattern*.—Pyramidal net pattern.

*Leaf size*.—180 mm (l)×120 mm (w).

*Abundance*.—Average.

*Texture*.—Leathery. Upper side of leaflet: Matte. Under side of leaflet: Matte.

*Color, mature foliage*.—Upper Leaf Surface: Yellow-Green Group 146A. Lower Leaf Surface: Yellow-Green Group 146B.

*Color, juvenile foliage*.—Upper Leaf Surface: Yellow-Green Group 144A. Lower Leaf Surface: Green Group 146C.

Stipules:

*Size*.—On average, 22 mm long and 4 mm between the tips of the stipules.

*Stipule color*.—Yellow-Green Group 146A.

*Anthocyanin*.—Located on upper surface and occasionally on lower surface of Greyed-Red Group 182D.

*Margins*.—Present in limited numbers, lightly pubescent on lower side.

*Shape*.—Apex: Apiculate. Base: Flat.

Petiole:

*Length*.—About 30-35 mm.

*Diameter*.—About 1.5 mm.

*Petiole color*.—Yellow-Green Group 146C.

*Underneath*.—With stipitate glands. Lightly pubescent.

*Margins*.—Occasional stipitate glands. Pubescent.

*Anthocyanin*.—Red Group 182C on upper side and margins.

*Prickles*.—Occasional prickles on lower surface of juvenile foliage.

Petiole rachis:

*Length*.—About 25-30 mm.

*Diameter*.—About 1.5 mm.

*Color*.—Yellow-Green Group 146C.

*Underneath*.—Rugose, with stipitate glands and occasional prickles.

*Margins*.—With stipitate glands.

*Anthocyanin*.—Light intonations of Greyed-Red Group 182C on upper side at point of leaflet attachment.

Leaflets:

*Size*.—Average size of the terminal leaflet is 60-80 mm (l)×40-50 mm (w).

*Shape*.—Entire leaflet: Ovate. Base: Obtuse. Apex: Acute.

*Margins*.—Finely serrated.

*Surface*.—Upper: Matte. Lower: Matte.

*Texture*.—Leathery.

Hips/seed formation: None observed.

Winter hardiness: To date, the variety has been grown successfully in USDA Zones 6-9.

Disease resistance: Good resistance to powdery mildew (*Sphaerotheca pannosa*), rust (*P. disciflorum*) and blackspot (*Diplocarpon rosae*), diseases under normal growing conditions.

Other distinguishing characteristics: Cultivar suitable for outdoor cut flower production.

I claim:

1. A new and distinct variety of rose plant, as described and illustrated herein.

* * * * *

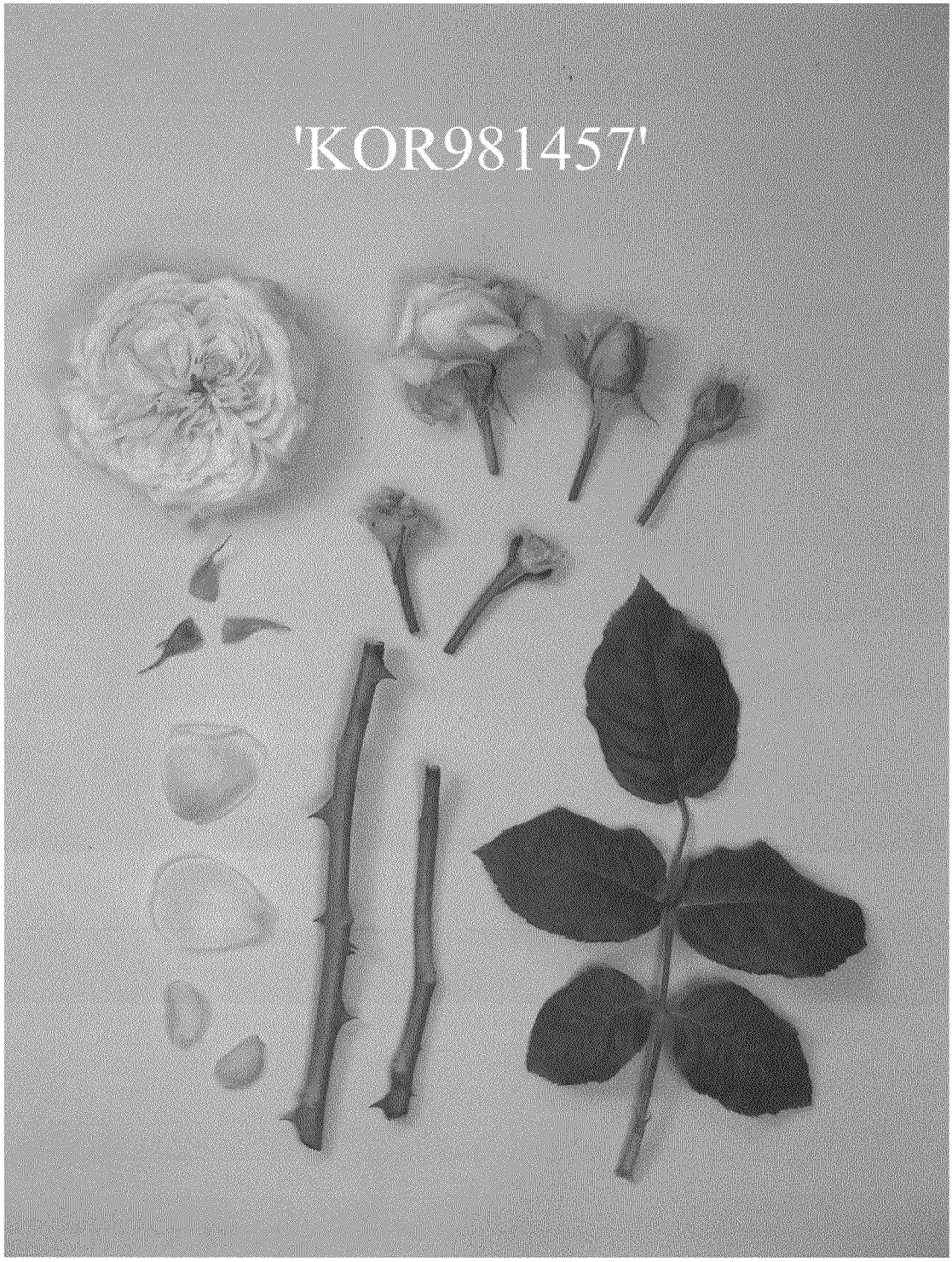
'KOR981457'